United States Patent [19]

Yoshida et al.

[11] 4,403,963
[45] Sep. 13, 1983

[54] FOUNDATION COMPOSITION SUITABLE FOR USE IN MAKING UP A MANNEQUIN

[75] Inventors: Jun Yoshida, Kamakura; Toshiharu Tsunemitsu, Yokohama; Masayoshi Nakano, Tokyo, all of Japan

[73] Assignee: Kanebo Cosmetics, Inc., Tokyo, Japan

[21] Appl. No.: 326,911

[22] Filed: Dec. 2, 1981

Related U.S. Application Data

[63] Continuation of Ser. No. 181,847, Aug. 27, 1980, abandoned.

[30] Foreign Application Priority Data

Aug. 31, 1979 [JP] Japan .............................. 54-111872

[51] Int. Cl.³ ........................................... G09B 25/00
[52] U.S. Cl. ................................. 434/100; 427/407.1
[58] Field of Search ............................ 434/100, 270; 427/407.1

[56] References Cited

U.S. PATENT DOCUMENTS 2,935,484  5/1960  Arnold et al. .................... 260/17 X
3,714,107  1/1973  Smith .................................. 106/72 X
3,926,894  12/1975  Clark ............................... 428/375 X

OTHER PUBLICATIONS

Kerr, Ralph W., *Chemistry and Industry of Starch*, 2nd Ed., Academic Press, Inc., N.Y., N.Y., 1950, pp. 14–17.

*Primary Examiner*—Michael R. Lusignan
*Attorney, Agent, or Firm*—Abelman, Frayne & Rezac

[57] ABSTRACT

A foundation composition useful in making-up a mannequin, comprising a polymeric film-forming material, a water-insoluble white powder material, the particles of which have an average size of from 2 to 100 microns and the content of which is in a range of from 20 to 60% based on the entire weight of the composition, and water. A method for making up said mannequin comprising undercoating the skin of said mannequin with said composition and a mannequin product of said method are claimed.

9 Claims, No Drawings

FOUNDATION COMPOSITION SUITABLE FOR USE IN MAKING UP A MANNEQUIN

This is a continuation of application Ser. No. 181,847 filed Aug. 27, 1980, now abandoned.

FIELD OF THE INVENTION

The present invention relates to a foundation composition suitable for use in making up a mannequin made of a synthetic resin.

BACKGROUND OF THE INVENTION

A mannequin (window dummy or lay figure) on which a cloth, a dress, a hat or a decorative accessory is placed, has been widely used in shop-fronts and show windows to attract the attention of customers and to tempt the customer to buy the goods shown on the mannequin.

Generally, such a mannequin is covered with a skin surface layer made of a synthetic resin so as to impart thereto a facial expression as close to that of a man or woman as possible, or to reduce the weight and cost of the mannequin. However, when the surface of the synthetic resin layer is to be made up with a conventional make-up material for the human body, the following difficulties are encountered.

1. The make-up material does not adhere to the surface of the skin layer and cannot be fixed on the surface of the skin to a satisfactory extent.
2. The make-up material cannot be uniformly spread on the surface of the skin layer of the mannequin and forms undesirable spots thereon.
3. The coloring matters contained in the make-up material dyes the skin layer of the mannequin, so that these matters remain on the surface layer of the mannequin after the make-up material is washed away. Accordingly, it is impossible to make up the mannequin with conventional make-up products for the human body.

An attempt has been made to make up mannequins with a paint. However, in this case, the resultant made-up skin surface exhibits an appearance significantly different from that of a commonly made-up skin of a human body. Also, it is extremely difficult to change the color of the painted skin surface to a desired color.

Under the above-mentioned circumstances, making-up of a mannequin has not been widely practiced, notwithstanding the fact that there is a strong desire to use mannequins suitably made-up for the dress or decorative goods placed on the mannequin.

On the other hand, in the sale of cosmetics at a store, frequently a beauty instructor or a customer acts as a model and makes up herself or himself with the cosmetics in order to demonstrate the effect of the cosmetics to the customer and to propagate them to the customer. A repeated making-up and washing of the face for such purposes is sometimes detrimental to the skin of the beauty instructor or customer. Also, when the customer is a model, it is difficult for the customer herself or himself to recognize the make-up effect resulting from the cosmetics. In some cases, the customer must wash the make-up, which causes inconvenience to the customer. Accordingly, there is a need for a process for making up a mannequin which is easy to carry out and allows the repeated make-up and washing operations to be applied to the mannequin.

As a result of extensive studies conducted by the present inventors, it has been discovered that, when a mannequin having a skin layer made of a synthetic resin is previously undercoated with a special foundation composition consisting essentially of a fine powdery material and a film-forming material, it becomes possible to make up the undercoated skin layer surface of the mannequin with a make-up material suitable for the human body in exactly the same manner as that used in making up the human body. From this discovery, the inventors have accomplished the present invention.

SUMMARY OF THE INVENTION

An object of the present invention is to provide a foundation composition which permits a mannequin to be made-up with a make-up material suitable for the human body.

Another object of the present invention is to provide a foundation composition which can be easily used to repeatedly make up a mannequin based on the purpose of the intended display.

Still another object of the present invention is to provide a foundation composition by which it is possible to carry out a demonstration of the make-up operation using a mannequin as a model.

The above-mentioned objects can be attained by the foundation composition of the present invention which is suitable for use in making up a mannequin and which comprises a polymeric film-forming material dispersed and/or dissolved in water, and a water-insoluble white powder material and water, the particles of the water-insoluble white powder material having an average size of from 2 to 100 microns, preferably, from 10 to 70 microns and the content of the water-insoluble white powder material being from 20 to 60% by weight, based on the entire weight of the composition.

DETAILED DESCRIPTION OF THE INVENTION

It is essential that the particles of the water-insoluble white powder material applicable to the present invention have an average size of from 2 to 100 microns. When the average particle size is less than 2 microns, the resultant foundation composition causes the make-up material used for the mannequin not to adhere to the skin layer surface of a mannequin undercoated with such a composition, or not to be fixed on the skin layer surface to a satisfactory extent. For this reason, such make-up material forms undesirable spots on the undercoated skin layer surface, i.e. the make-up material cannot be uniformly spread on the skin layer surface of the mannequin. On the other hand, in the case where the average size of the particles of the white powder material is more than 100 microns, the resultant foundation composition prevents the make-up material from being uniformly deposited or smoothly spread on the undercoated skin layer surface and tends to form undesirable spots of the make-up material thereon.

The water-insoluble white powder material usable for the present invention can be selected from the group consisting of natural or semi-synthetic polymeric powder materials, for example, β-type starch particles, cellulose powders, cellulose acetate powders, cellulose butyrate powders, silk powders and wool powders; synthetic polymeric powders, for example, polyvinyl chloride powders, polystyrene powders and nylon powders; metal soap powders, for example, zinc stearate, magnesium myristate and zinc laurate; extender pigments (bodies), for example, talc, kaolin, calcium carbonate, magnesium carbonate, barium sulfate, aluminum hydroxide, alumina, powdery silica, mica and diatomaceous earth; white pigments, for example, titanium dioxide, zinc flour, antimony trioxide, white lead, basic lead sulfate and zinc sulfide.

Commercially available white pigments are generally composed of fine particles having an average size of less than 2 microns due to the increased covering property thereof. Accordingly, it is to be noted that these commercially available white pigments are not applicable to the present invention. Preferred water-insoluble white powder materials usable for the present invention are $\beta$-type starch particles, talc, kaolin and aluminum hydroxide.

The water-insoluble white powder material is used in an amount of from 20 to 60% by weight, preferably, from 30 to 50% by weight, based on the entire weight of the foundation composition. When the content of the water-insoluble white powder material is less than 20% by weight, the resultant foundation composition causes the make-up material applied onto the mannequin to slip off from the skin layer surface of the mannequin undercoated with the composition or to be unevenly deposited and not uniformly spread on the undercoated surface. On the other hand, when the content of the water-insoluble white powder material is more than 60% by weight, the resultant foundation composition exhibits a poor spreading property, which causes the skin layer surface of a mannequin to be unevenly undercoated and the undercoated surface to be coarse, and results in a reduced bonding property of the water-insoluble white powder material to the skin layer surface of the mannequin. Accordingly, when a mannequin undercoated with the above-mentioned foundation composition is made-up, with conventional make-up material for the human body, the made-up surface of the mannequin becomes coarse and spotty, and therefore, a beautiful make-up finish cannot be attained.

The polymeric film-forming material usable for the present invention is used in the form of an aqueous dispersion and/or solution. The polymeric film-forming material which is used in the form of an aqueous dispersion can be selected from vinyl resins in the form of an emulsion and synthetic rubbers in the form of a latex which have generally been produced by an emulsion polymerization method. Examples of such vinyl resins and synthetic rubbers are vinyl acetate-based resins, vinyl chloride-based resins, vinylidene chloride-based resins, acrylic or methacrylic lower ester-based resins, styrene-butadiene copolymer-based rubbers, and nitrile rubbers obtained from the copolymerization of acrylonitrile and butadiene. The polymeric film-forming material which is used in the form of an aqueous solution can be selected from natural and semi-synthetic water-soluble polymers, for example, gum arabic, casein, dextrin, pectin, sodium alginate, $\alpha$-type starch, methyl cellulose, carboxymethyl cellulose and hydroxyethyl cellulose, and; synthetic water-soluble polymers, for example, polyvinyl alcohol, polyvinyl pyrrolidone, sodium polyacrylate and carboxyvinyl polymers. The water-soluble polymer may be used, as required, in conjunction with the above-mentioned emulsion type vinyl resins or latex type synthetic rubbers in order to increase the viscosity or stability of the resultant aqueous solution. However, because the water-soluble polymer exhibits a poor resistance to water, it is preferable that the above-mentioned emulsion type vinyl resins or latex type synthetic rubbers be used as a polymeric film-forming material for the foundation composition of the present invention. That is, in the case where the skin layer surface of a mannequin is undercoated with a foundation composition, whose film-forming material consists of a water-soluble polymer, prior to the application of the make-up material for a human body, and if the make-up material for a human body is oily cosmetics, such as the w/o type foundations, lipstick and eye shadow, or anhydrous cosmetics, such as a face powder and a cheek rouge, the object of the present invention can be satisfactorily attained. However, if the make-up material is an aqueous cosmetic, such as o/w type foundations, a film of the water-soluble polymeric material formed on the surface of the mannequin is easily separated and removed from the surface during the make-up operation. Therefore, it is impossible to make up the undercoated surface with the aqueous cosmetics. Contrary to this, a foundation composition where the polymeric film-forming material consists of an emulsion type vinyl resin or a latex type synthetic rubber, this may be applied to a mannequin irrespective of the type of make-up material to be used. A more preferable film-forming material is a vinyl acetate-based resin in the form of an emulsion.

The polymeric film-forming material firmly adheres in the form of a thin film to the skin layer surface of the mannequin which is made of a synthetic resin, and fixes the above-mentioned water-insoluble white powder material onto the skin layer surface. The content of the polymeric film-forming material in the foundation composition of the present invention may be variable as long as the above-mentioned effects can be attained. That is, when the content of the polymeric film-forming material in the foundation composition is too small, the water-insoluble white powder material cannot be satisfactorily fixed on the skin layer surface of a mannequin. Accordingly, when the mannequin undercoated by the foundation composition is made up with a make-up material for the human body, the make-up operation causes the water-insoluble white powder material to be easily separated from the skin layer surface of the mannequin. Therefore, the make-up material cannot be firmly fixed on the undercoated skin layer surface and is easily removed therefrom.

On the other hand, an excessively high content of the polymeric film-forming material in the foundation composition results in an extreme increase in the viscosity of the resultant foundation composition, which causes the spreading property of the foundation composition on the skin layer surface of the mannequin to be remarkably poor, and the made-up surface to be uneven. For this reason, the application of make-up material for the human body onto the skin layer surface of a mannequin undercoated with such a foundation composition results in an undesirable finishing effect. Preferably, the content of the polymeric film-forming material in the foundation composition of the present invention is in the range of from 1 to 35% by weight, based on the weight of the composition.

The foundation composition of the present invention comprises, as an essential component, the polymeric film-forming material, the water-insoluble white powder material and water. The foundation composition may contain, if desired, an additive selected from, for example, emulsifying agents or dispersion stabilizers, surface active agents, thickeners, bactericides, preservatives, perfumes, plasticizers and solvents for the above-mentioned materials.

The foundation composition of the present invention contains a large amount of the water-insoluble white powder material, the particles of which have a relatively large size, and the water-insoluble white powder material generally exhibits a specific gravity higher than that of the dispersing and/or dissolving medium. Accordingly, if the foundation composition of the present invention is prepared in such a manner that the resultant dispersion and/or solution exhibits a low viscosity, the water-insoluble white powder material tends to deposit therefrom. Therefore, it is preferable that the foundation composition of the present invention be prepared in the form of a paste containing a thickener.

When a mannequin with a skin layer made of a synthetic resin is undercoated with the foundation composition of the present invention, the undercoated mannequin skin surface can be easily made up with make-up material for the human body so that it has the same beautiful make-up finish as that obtained on a human body. This effect of the foundation composition of the present invention is clearly different from that of the conventional paint coating process. The foundation composition of the present invention makes it possible to make up a mannequin easily and repeatedly with the make-up material for a human body, and to attain a beautiful and natural make-up finish effect. This feature is effective for further increasing the utility of a mannequin displayed in a shop-front or a show window, because the use of the foundation composition of the present invention makes it possible to easily make up the mannequin based on the dress or decorative goods placed on the mannequin or the background against which the mannequin is placed. In addition, in the propaganda and sale of cosmetics at a store, the use of the foundation composition of the present invention allows the necessity of adopting a beauty instructor or a customer as a model for the make-up operations to be dispensed with. The use of the foundation composition of the present invention is effective in allowing the make-up instructor to avoid the detrimental effect of repeated use of the make-up material on the skin of the beauty instructor.

The present invention will be illustrated by the examples set forth below. However, it will be understood that these examples are only illustrative and in no way limit the scope of the present invention.

EXAMPLE 1

1.8 Parts by weight of a preservative consisting of a mixture of methyl p-hydroxybenzoate, ethyl p-hydroxybenzoate and sodium dihydroacetate in an equal weight were dissolved in 16.0 parts by weight of propylene glycol. The resultant solution was added to 81.0 parts by weight of an aqueous emulsion containing 43.1% by weight of polyvinyl acetate. Then, the resultant mixture was admixed with 1.2 parts by weight of a thickener (the trademark of which was AEROSIL made by Nippon Aerosil Co., Japan), while the mixture was stirred.

Next, 60 parts by weight of the liquid admixture thus prepared were uniformly mixed with 40 parts by weight of white alumina, titanium dioxide or zinc oxide, the particles of which had an average size as indicated in Table 1, to prepare a paste-like foundation composition for a mannequin. The mixing was carried out at room temperature.

A mannequin, whose skin layer consisted of polyvinyl chloride, was undercoated with the above-prepared foundation composition by brush coating. After the undercoating was dried, the mannequin was made-up with a make-up cosmetic for the human body. The results are shown in Table 1. After the making-up was completed, the make-up cosmetic and the foundation composition could be easily wiped off by using a cloth impregnated with a 50% aqueous solution of ethyl alcohol or a face cleansing liquid.

TABLE 1

| Type of water insoluble white powder material | Average size of particles (microns) | Makingup effect obtained by makingup cosmetic |
|---|---|---|
| Titanium dioxide | 0.4 | Cosmetic did not adhere and no fixation of cosmetic occurred. |
| Zinc oxide | 0.6 | Cosmetic did not adhere and no fixation of cosmetic occurred. |
| White alumina | 4 | Cosmetic slightly adhered and a slightly uneven fixation of cosmetic occurred. |
| White alumina | 10 | Cosmetic were satisfactorily fixed and a beautiful make-up finish was attained. |
| White alumina | 70 | Cosmetic were satisfactorily fixed and a beautiful make-up finish was attained. |
| White alumina | 100 | Spread of cosmetic was slightly poor and a slightly uneven fixation of cosmetic occurred. |
| White alumina | 125 | Spread of cosmetics was very poor and a substantially uneven fixation of cosmetic occurred. |

EXAMPLE 2

A polyvinyl acetate liquid mixture which was prepared in the same manner as that in Example 1, was admixed with cornstarch or talc in the proportion indicated in Table 2, at room temperature, to prepare a foundation composition for a mannequin. The particles of cornstarch and talc had average sizes of 15 microns and 18 microns, respectively.

The same mannequin as used in Example 1 was undercoated with the above-prepared foundation composition by means of a brush coating. After the undercoating was dried, the mannequin was made-up with a make-up cosmetic for the human body. The results are shown in Table 2.

TABLE 2

| Type of water-insoluble powder material | Mixing ratio (part by weight) | | Coating property of foundation compostion | Make-up effect obtained by making-up cosmetic |
|---|---|---|---|---|
| | Water-insoluble white powder material | Liquid mixture | | |
| Cornstarch | 10 | 90 | Uniformly coated. | Cosmetic slipped off. |
| Cornstarch | 20 | 80 | Uniformly coated. | Fixation of cosmetic was excellent and beautiful make-up |

TABLE 2-continued

| Type of water-insoluble powder material | Mixing ratio (part by weight) | | Coating property of foundation compostion | Make-up effect obtained by making-up cosmetic |
|---|---|---|---|---|
| | Water-insoluble white powder material | Liquid mixture | | |
| Cornstarch | 50 | 50 | Uniformly coated. | finish was obtained. Fixation of cosmetic was excellent and beautiful make-up finish was obtained. |
| Cornstarch | 60 | 40 | Spread of foundation composition was slightly poor so that the composition had to be carefully coated. | Sometimes, uneven fixation of cosmetic occurred |
| Cornstarch | 70 | 30 | Spread of foundation composition was very poor so that uniform coating was impossible. | Remarkably uneven fixation of cosmetic occurred. |
| Talc | 10 | 90 | Uniformly coated. | No cosmetic adhered. |
| Talc | 20 | 80 | Uniformly coated. | Cosmetic slightly adhered so that making-up had to be carefully carried out. |
| Talc | 30 | 70 | Uniformly coated. | Fixation of cosmetic was excellent and beautiful make-up finish was obtained. |
| Talc | 60 | 40 | Uniformly coated. | Fixation of cosmetic was excellent and beautiful make-up finish was obtained. |
| Talc | 70 | 30 | Spread of foundation composition was very poor so that uniform coating was impossible. | Remarkable uneven fixation of cosmetic occurred. |

Instead of the above-mentioned mannequin, a film shaped material or plate-shaped material consisting of a member selected from the group consisting of a polystyrene, an acrylonitrile-styrene resin, an acrylonitrile-butadiene-styrene resin, a polyethylene terephthalate, an acrylic resin, a polycarbonate, a cellulose acetate resin, a polyisoprene, a butadiene rubber and a neoprene rubber, was undercoated with the above-mentioned formulation composition containing 50% by weight of cornstarch and, then, the resultant undercoated material was made-up with a make-up cosmetic for the human body. In every case, a beautiful make-up finish effect was obtained.

EXAMPLE 3

1.1 Parts by weight of the preservative used in Example 1 was dissolved in 10.0 parts by weight of propylene glycol. The resultant solution was added to 53.5 parts by weight of an aqueous emulsion containing 45% by weight of polyvinyl chloride, while the resultant mixture was stirred. Next, 1.0 part by weight of the Aerosil 200 used in Example 1 and 34.4 parts by weight of the cornstarch used in Example 2 were added to the mixture and the resultant mixture was stirred at room temperature.

The mannequin used in Example 1 was undercoated with the above-mentioned prepared foundation composition by means of brush coating. After the undercoating was dried, the mannequin was made-up with a make-up cosmetic for the human body. A beautiful make-up finish was obtained without causing any uneven fixation of the cosmetic.

EXAMPLE 4

1.1 Parts by weight of the same preservative as used in Example 1 was dissolved in 10.0 parts by weight of propylene glycol. The resultant solution was added to 52.5 parts by weight of a latex containing 43.9% by weight of a styrene-butadiene rubber and the resultant mixture was stirred. Next, 2.0 parts by weight of the same thickener as used in Example 1 and 34.4 parts by weight of the same cornstarch as used in Example 2 were added to the mixture and, then, the resultant mixture was stirred.

Finally, the same procedures as those described in Example 3 were repeated using the above-mentioned prepared foundation composition. A beautiful make-up finish was obtained on a mannequin.

EXAMPLE 5

0.6 Part by weight of the same preservative as that used in Example 1 was dissolved in 10.0 parts by weight of propylene glycol. The resultant solution was added to 46.0 parts by weight of Jellymar AT-210 containing 30% by weight of an acrylic water-soluble resin manufactured by Nippon Junyaku Co. and the resultant mixture was stirred. Next, 8.4 parts by weight of water, 1.0 part by weight of the same thickener as used in Example 1 and 34.0 parts by weight of the cornstarch used in Example 2 were added to the mixture and stirred at room temperature.

The mannequin used in Example 1 was undercoated with the above-mentioned prepared foundation composition. After the undercoating was dried, the mannequin was made-up with a make-up cosmetic for the human body. In the case where the make-up cosmetic was oily or anhydrous in nature, a beautiful make-up finish could be obtained. However, when the make-up cosmetic consisted of aqueous materials, such as o/w type foundations, the undercoated layer was separated and removed from the skin layer surface during the make-up operation, so that a uniform make-up effect could not be attained.

EXAMPLE 6

11.1 Parts by weight of the propylene glycol solution containing the preservative used in Example 3 was added to 61.9 parts by weight of a polyvinyl acetate emulsion having a concentration of polyvinyl acetate of 41.1% by weight and the resultant mixture was stirred. Next, 26.0 parts by weight of nylon powders, the particles of which had an average size of 20 microns, and 1.0 part by weight of calcium bicarbonate powders, the particles of which had an average size of 13 microns, were added to the mixture and the resultant mixture was stirred to prepare a foundation composition according to the present invention. The resultant foundation composition allowed a mannequin to be uniformly made-up with a conventional make-up cosmetic for the human body.

EXAMPLE 7

11.1 Parts by weight of the propylene glycol solution containing the preservative used in Example 3 was added to 63.6 parts by weight of a polyvinyl acetate emulsion having a concentration of polyvinyl acetate of 43.0% by weight and the resultant mixture was stirred. Then, 25.3 parts by weight of magnesium bicarbonate powder having an average particle size of 15 microns was added to the mixture and the resultant mixture was stirred to prepare a foundation composition according to the present invention. The resultant foundation composition allowed a mannequin to be uniformly made-up with a conventional make-up cosmetic for the human body.

EXAMPLE 8

A foundation composition according to the present invention was prepared according to the same procedures as those described in Example 7, except that 23.7 parts by weight of zinc stearate powders, having an average particle size of 18 microns, and 1.6 parts by weight of the same calcium bicarbonate as that used in Example 6 were substituted for 25.3 parts by weight of the magnesium bicarbonate used in Example 7. The same result as that described in Example 7 was obtained.

EXAMPLE 9

11.1 Parts by weight of the propylene glycol solution containing the preservative used in Example 3 was added to 52.8 parts by weight of a polyvinyl acetate emulsion having a concentration of polyvinyl acetate of 44.3% by weight and the resultant mixture was stirred. Next, 34.7 parts by weight of kaolin powders, the particles of which had an average size of 6 microns, or aluminum hydroxide powders, the particles of which had an average size of 25 microns, and 1.4 parts by weight of the same calcium bicarbonate as used in Example 6 were added to the above-prepared mixture and the resultant mixture was stirred to prepare a foundation composition according to the present invention. The same result as that mentioned in Example 7 was obtained.

What is claimed is:

1. A method for making-up an artificial mannequin with a make-up material for a human body, comprising undercoating a skin surface layer of an artificial mannequin made from a synthetic resin, with a foundation composition which comprises a dispersion or solution of a polymeric film-forming material in water, a water-insoluble white powder material and water, the particles of said water-insoluble white powder material having an average size of from 2 to 100 microns, and the content of said water-insoluble white powder material being in a range of from 20 to 60 based on the entire weight of said composition, and making up said undercoated skin surface layer with the make-up material for a human body.

2. The method as claimed in claim 1, wherein said water-insoluble white powder material is selected from the group consisting of polymeric powders, and extender pigments consisting of inorganic compounds and metal soap powders.

3. The method as claimed in claim 2, wherein said polymeric powder consists of $\beta$-type starch particles.

4. The method as claimed in claim 2, wherein said extender pigment consists of at least one member selected from the group consisting of talc, kaolin and aluminum hydroxide.

5. The method as claimed in claim 1, wherein said polymeric film-forming material is in the form of an emulsion or a latex.

6. The method as claimed in claim 5, wherein said emulsion contains at least one resin selected from the group consisting of vinyl acetate resins and vinyl chloride resins.

7. The method as claimed in claim 5, wherein said latex contains a styrene-butadiene rubber.

8. The method as claimed in claim 1, wherein the content of said polymeric film-forming material is in the range of from 1 to 35% by weight.

9. An artificial mannequin having a skin surface layer of a synthetic resin and made up by the method as claimed in claim 1.

* * * * *